United States Patent
Emery et al.

(10) Patent No.: US 9,827,031 B2
(45) Date of Patent: Nov. 28, 2017

(54) DISC SPACE SIZING DEVICES

(75) Inventors: Jeffrey L. Emery, Emerald Hills, CA (US); Mark Y. Hirotsuka, San Jose, CA (US); J. Brook Burley, Mountain View, CA (US)

(73) Assignee: Benvenue Medical, Inc., Santa Clara, CA (US)

( * ) Notice: Subject to any disclaimer, the term of this patent is extended or adjusted under 35 U.S.C. 154(b) by 176 days.

(21) Appl. No.: 13/700,178

(22) PCT Filed: May 27, 2011

(86) PCT No.: PCT/US2011/038377
§ 371 (c)(1),
(2), (4) Date: Jan. 22, 2013

(87) PCT Pub. No.: WO2011/150350
PCT Pub. Date: Dec. 1, 2011

(65) Prior Publication Data
US 2013/0144388 A1    Jun. 6, 2013

Related U.S. Application Data

(60) Provisional application No. 61/349,587, filed on May 28, 2010.

(51) Int. Cl.
*A61F 2/44* (2006.01)
*A61B 17/88* (2006.01)
(Continued)

(52) U.S. Cl.
CPC ........ *A61B 17/8852* (2013.01); *A61B 17/025* (2013.01); *A61B 17/885* (2013.01);
(Continued)

(58) Field of Classification Search
CPC ..... A61B 17/02; A61B 17/025; A61B 17/885; A61B 17/8852; A61B 17/8858;
(Continued)

(56) References Cited

U.S. PATENT DOCUMENTS 4,863,476 A * 9/1989 Shepperd ............... 623/17.15
5,445,639 A * 8/1995 Kuslich et al. ............. 606/80
(Continued)

FOREIGN PATENT DOCUMENTS

WO    WO 03/024344 A1    3/2003

OTHER PUBLICATIONS

International Search Report and Written Opinion for PCT Appl'n. No. PCT/US2011/038377, dated Aug. 25, 2011.
(Continued)

*Primary Examiner* — Matthew Lawson
*Assistant Examiner* — Amy Sipp
(74) *Attorney, Agent, or Firm* — Cook Alex Ltd.

(57) ABSTRACT

A spacing device is provided for adjusting or measuring the spacing between adjacent vertebral bodies. The spacing device has a distal end with at least one distraction member adapted for insertion into an intervertebral disc space and movable between a low profile first configuration and a higher profile second configuration. Also provided is an actuator for moving the distraction member between the first configuration (for delivery of the distal end of the spacing device to a target disc space) and the second configuration (for manipulation or measurement of the space between adjacent vertebral bodies).

18 Claims, 9 Drawing Sheets

(51) Int. Cl.
*A61B 17/02* (2006.01)
*A61B 17/29* (2006.01)
*A61F 2/30* (2006.01)
*A61F 2/46* (2006.01)

(52) U.S. Cl.
CPC ............ *A61F 2/442* (2013.01); *A61F 2/4455* (2013.01); *A61B 2017/0256* (2013.01); *A61B 2017/2933* (2013.01); *A61B 2017/2941* (2013.01); *A61B 2017/2943* (2013.01); *A61F 2002/30579* (2013.01); *A61F 2002/4658* (2013.01)

(58) Field of Classification Search
CPC .... A61B 2017/0256; A61B 2017/0262; A61B 2017/0268; A61F 2/4455; A61F 2/447
See application file for complete search history.

(56) References Cited

U.S. PATENT DOCUMENTS

| | | | |
|---|---|---|---|
| 5,755,661 A * | 5/1998 | Schwartzman | 600/216 |
| 6,332,895 B1 * | 12/2001 | Suddaby | 623/17.11 |
| 6,454,806 B1 * | 9/2002 | Cohen | A61F 2/4455 |
| | | | 623/17.15 |
| 7,824,445 B2 * | 11/2010 | Biro | A61F 2/44 |
| | | | 623/17.15 |
| 8,252,001 B2 | 8/2012 | Quirno et al. | |
| 8,628,577 B1 * | 1/2014 | Jimenez | A61F 2/447 |
| | | | 623/17.15 |
| 8,974,464 B2 * | 3/2015 | Johnson et al. | 606/90 |
| 8,979,860 B2 * | 3/2015 | Voellmicke et al. | 606/99 |
| 8,986,385 B2 * | 3/2015 | Hall | 623/17.11 |
| 9,034,041 B2 * | 5/2015 | Wolters et al. | 623/17.15 |
| 9,039,771 B2 * | 5/2015 | Glerum et al. | 623/17.16 |
| 2001/0029377 A1 | 10/2001 | Aebi et al. | |
| 2002/0128716 A1 * | 9/2002 | Cohen | A61F 2/44 |
| | | | 623/17.15 |
| 2003/0083747 A1 * | 5/2003 | Winterbottom et al. | 623/17.11 |
| 2003/0158553 A1 * | 8/2003 | Michelson | 606/61 |
| 2003/0187453 A1 * | 10/2003 | Schlapfer et al. | 606/90 |
| 2003/0220650 A1 * | 11/2003 | Major et al. | 606/90 |
| 2003/0236520 A1 * | 12/2003 | Lim | A61B 17/025 |
| | | | 606/99 |
| 2004/0087994 A1 * | 5/2004 | Suddaby | 606/190 |
| 2004/0102774 A1 * | 5/2004 | Trieu | 606/61 |
| 2004/0193158 A1 * | 9/2004 | Lim | A61B 17/025 |
| | | | 606/99 |
| 2004/0230198 A1 * | 11/2004 | Manzi et al. | 606/90 |
| 2005/0065610 A1 * | 3/2005 | Pisharodi | 623/17.13 |
| 2005/0080425 A1 * | 4/2005 | Bhatnagar | A61B 17/02 |
| | | | 606/90 |
| 2005/0182416 A1 * | 8/2005 | Lim | A61B 17/025 |
| | | | 606/90 |
| 2005/0234493 A1 * | 10/2005 | Carr et al. | 606/181 |
| 2005/0261683 A1 * | 11/2005 | Veldhuizen et al. | 606/61 |
| 2006/0058876 A1 * | 3/2006 | McKinley | A61F 2/4611 |
| | | | 623/17.11 |
| 2006/0116689 A1 | 6/2006 | Albans | |
| 2006/0189999 A1 * | 8/2006 | Zwirkoski | 606/90 |
| 2006/0224241 A1 * | 10/2006 | Butler et al. | 623/17.15 |
| 2006/0287727 A1 * | 12/2006 | Segal et al. | 623/17.12 |
| 2007/0123903 A1 | 5/2007 | Raymond et al. | |
| 2007/0149978 A1 * | 6/2007 | Shezifi et al. | 606/90 |
| 2007/0233143 A1 * | 10/2007 | Josse et al. | 606/90 |
| 2007/0260315 A1 * | 11/2007 | Foley et al. | 623/17.12 |
| 2007/0276406 A1 * | 11/2007 | Mahoney | A61B 17/025 |
| | | | 606/106 |
| 2008/0114367 A1 * | 5/2008 | Meyer | 606/90 |
| 2008/0177259 A1 * | 7/2008 | Wu | 606/57 |
| 2008/0183204 A1 * | 7/2008 | Greenhalgh et al. | 606/198 |
| 2008/0300636 A1 * | 12/2008 | Carli et al. | 606/280 |
| 2009/0005784 A1 * | 1/2009 | Blain et al. | 606/90 |
| 2009/0024217 A1 * | 1/2009 | Levy et al. | 623/17.16 |
| 2009/0105711 A1 * | 4/2009 | Mitchell | 606/92 |
| 2010/0114179 A1 * | 5/2010 | Moore et al. | 606/308 |
| 2010/0185291 A1 * | 7/2010 | Jimenez | F16C 11/12 |
| | | | 623/17.16 |
| 2011/0015638 A1 * | 1/2011 | Pischl | A61B 17/025 |
| | | | 606/90 |
| 2011/0015747 A1 * | 1/2011 | McManus et al. | 623/17.16 |
| 2011/0172722 A1 * | 7/2011 | Verhulst et al. | 606/86 A |
| 2012/0071977 A1 * | 3/2012 | Oglaza et al. | 623/17.11 |
| 2012/0089231 A1 * | 4/2012 | Prestigiacomo | 623/17.16 |
| 2012/0123426 A1 | 5/2012 | Quirno | |
| 2012/0136448 A1 * | 5/2012 | Seifert et al. | 623/17.16 |
| 2012/0150241 A1 * | 6/2012 | Ragab et al. | 606/86 A |
| 2013/0053863 A1 * | 2/2013 | Juravic et al. | 606/119 |
| 2013/0116791 A1 * | 5/2013 | Theofilos | 623/17.16 |
| 2013/0144388 A1 * | 6/2013 | Emery et al. | 623/17.16 |
| 2013/0144391 A1 * | 6/2013 | Siegal et al. | 623/17.12 |
| 2013/0158667 A1 * | 6/2013 | Tabor et al. | 623/17.16 |
| 2014/0135776 A1 * | 5/2014 | Huffmaster et al. | 606/90 |
| 2014/0249629 A1 * | 9/2014 | Moskowitz et al. | 623/17.15 |
| 2014/0257484 A1 * | 9/2014 | Flower et al. | 623/17.15 |
| 2015/0051701 A1 * | 2/2015 | Glerum et al. | 623/17.16 |
| 2015/0100124 A1 * | 4/2015 | Whipple | 623/17.15 |
| 2015/0112437 A1 * | 4/2015 | Davis et al. | 623/17.15 |
| 2015/0112438 A1 * | 4/2015 | McLean | 623/17.16 |
| 2015/0148908 A1 * | 5/2015 | Marino et al. | 623/17.16 |

OTHER PUBLICATIONS

International Search Report and Written Opinion for PCT Patent Appl'n. No. PCT/US2013/068906, dated Feb. 6, 2014.
Extended European Search Report for European Patent Appl'n. No. 11787510.4, dated Oct. 15, 2013.

* cited by examiner

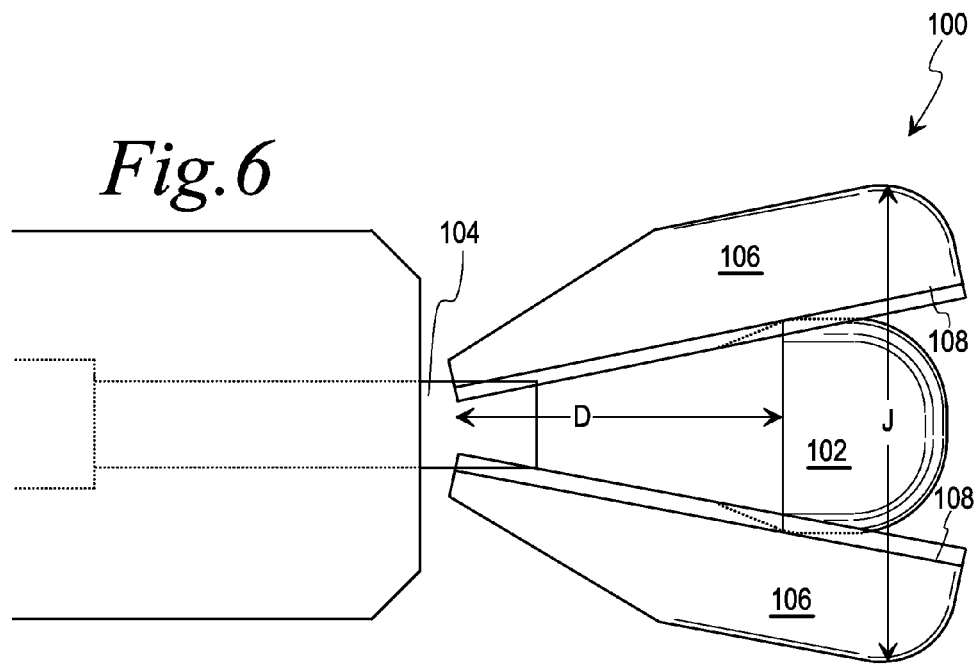
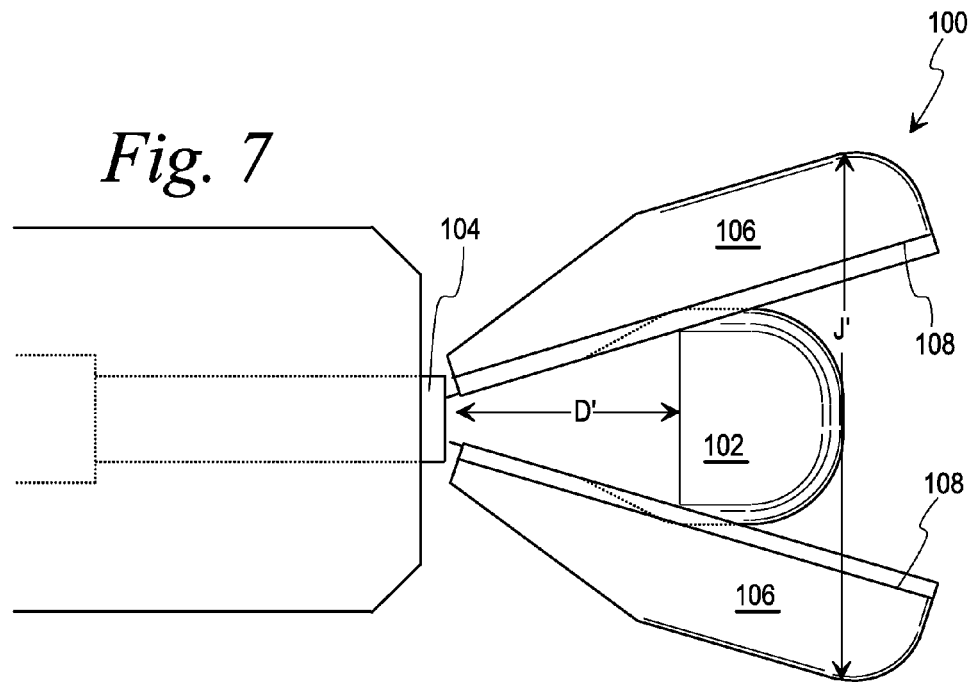

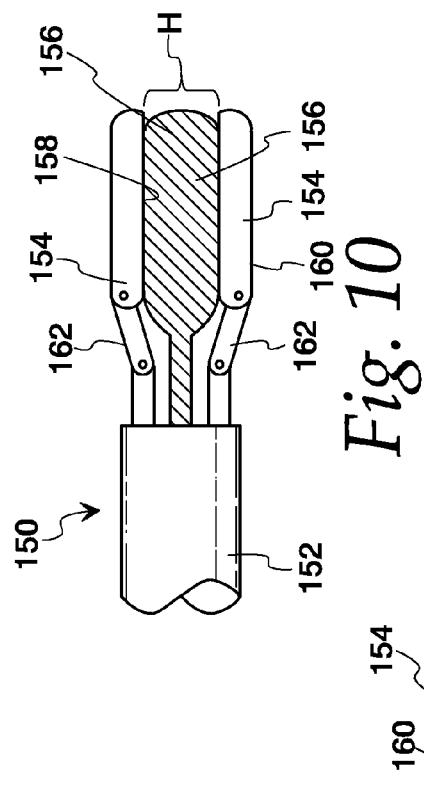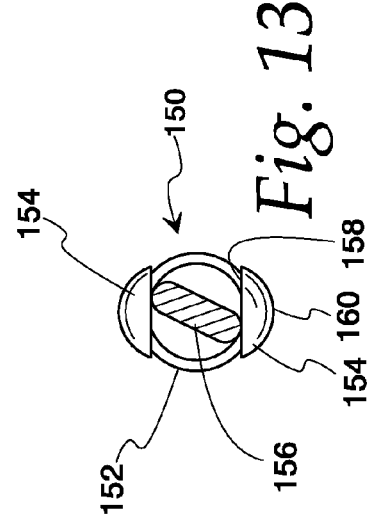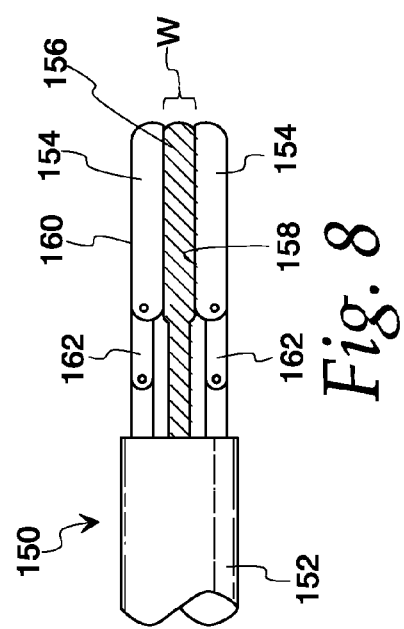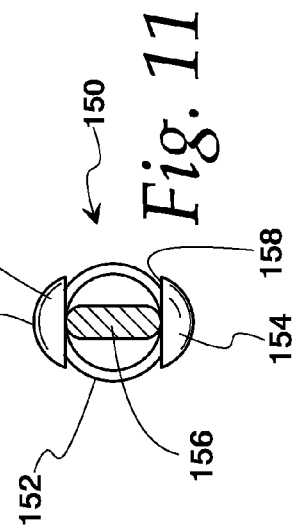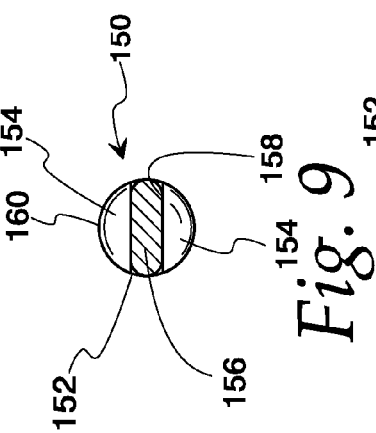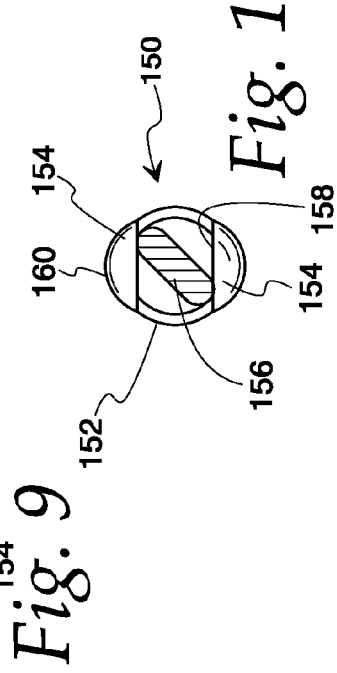
Fig. 8
Fig. 9
Fig. 10
Fig. 11
Fig. 12
Fig. 13

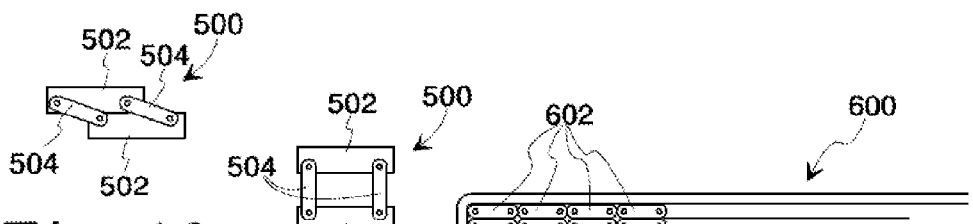
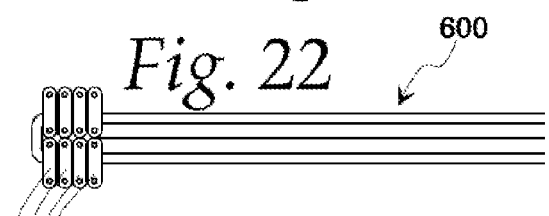
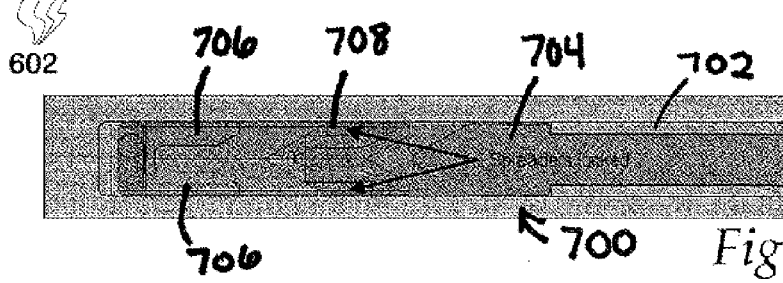
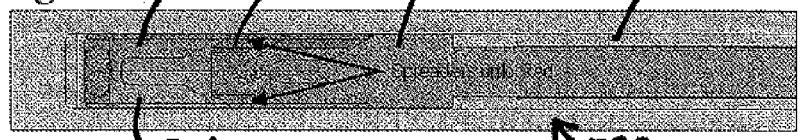
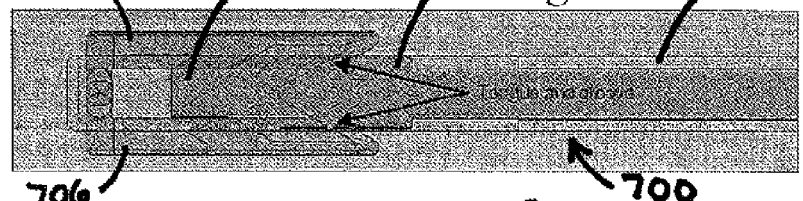
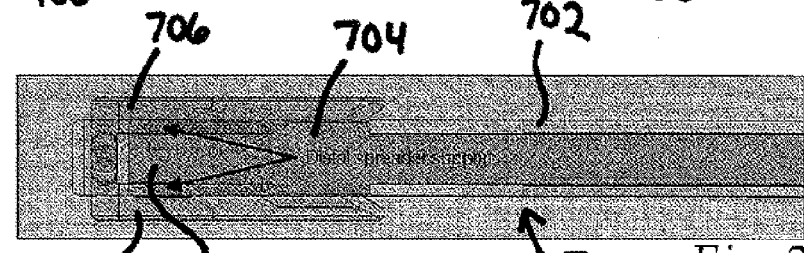

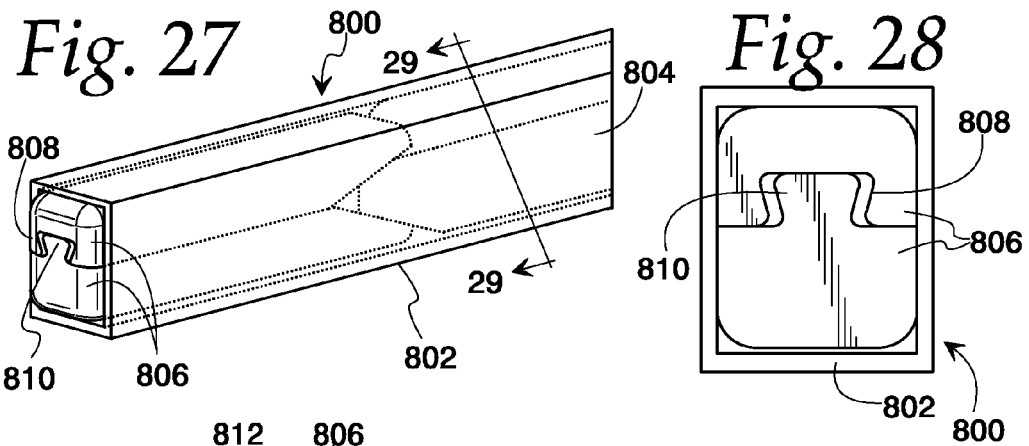
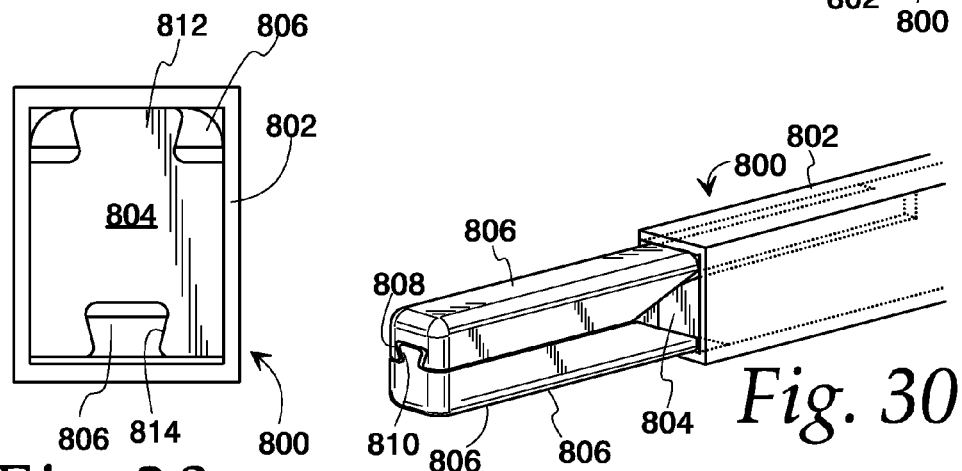
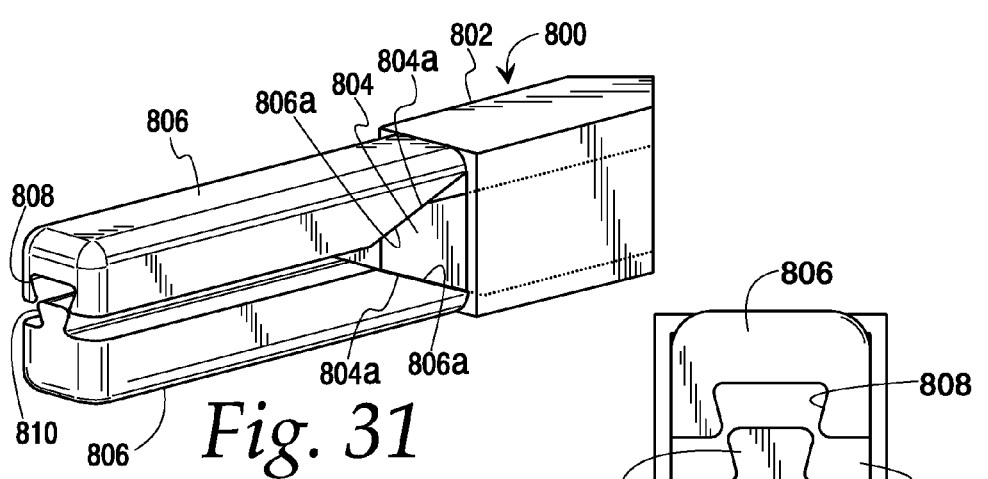

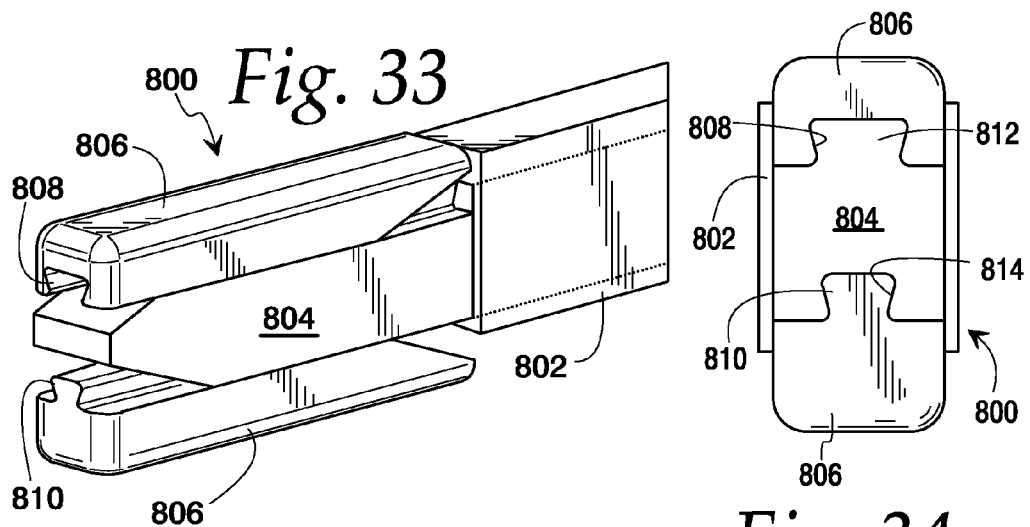
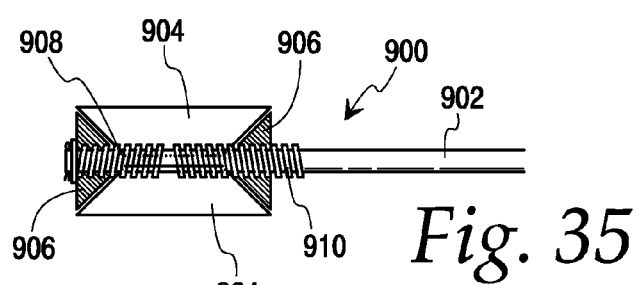
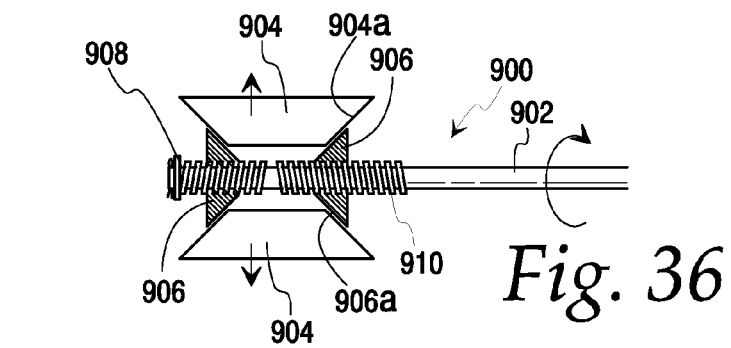

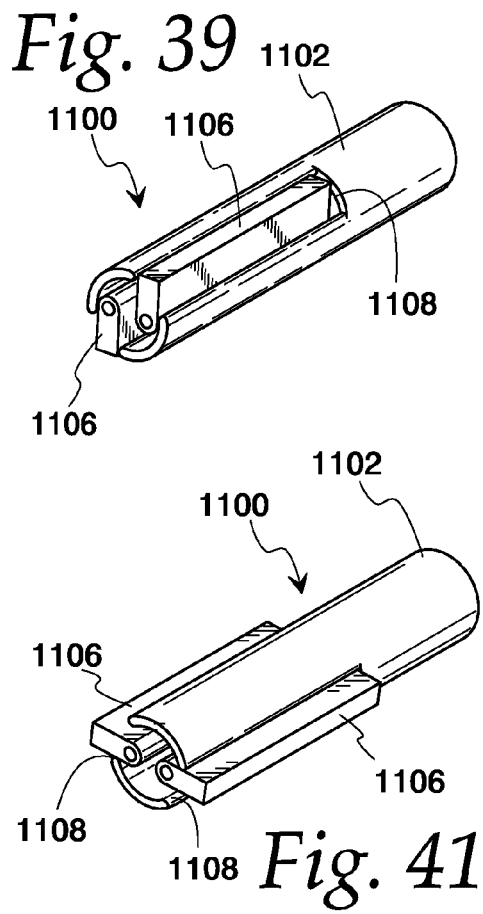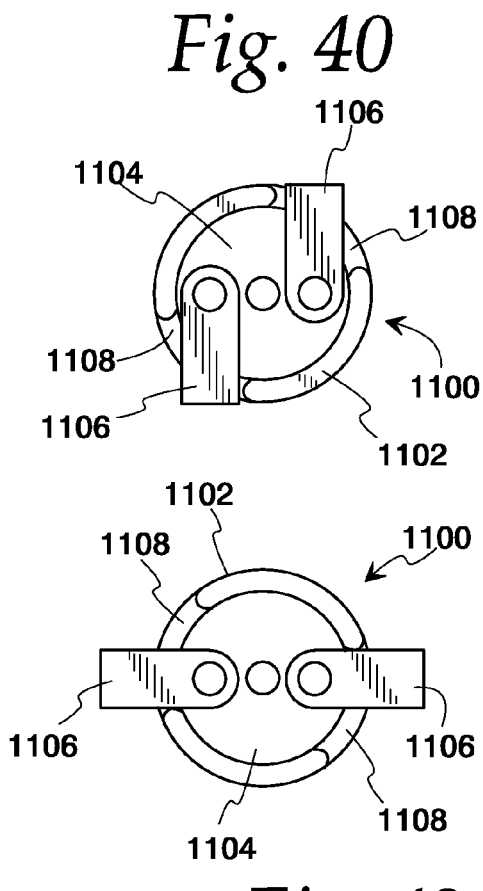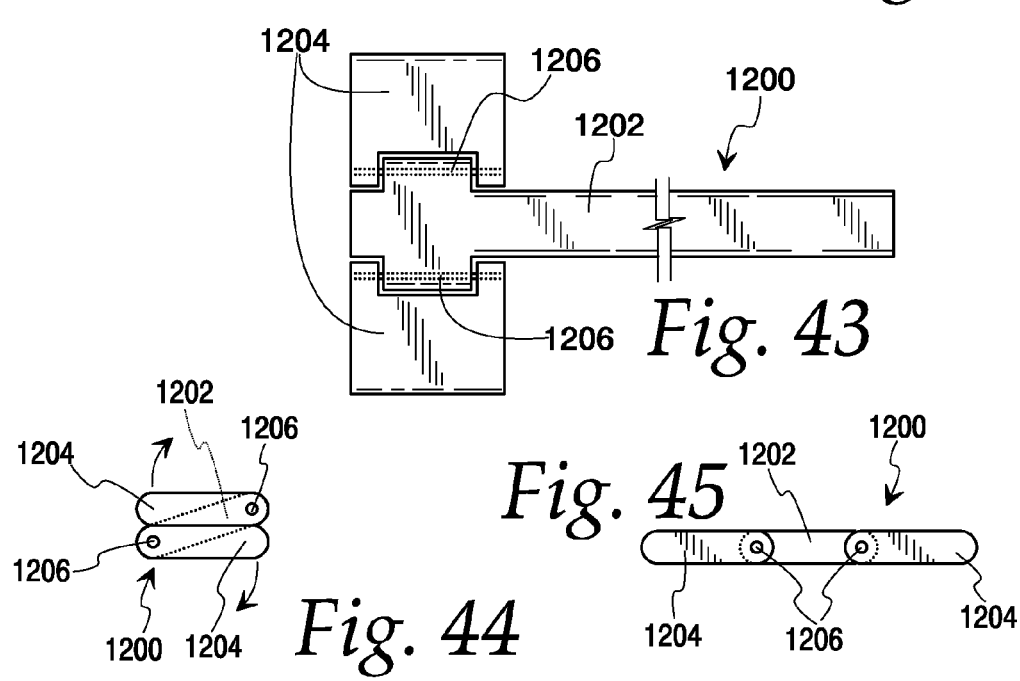

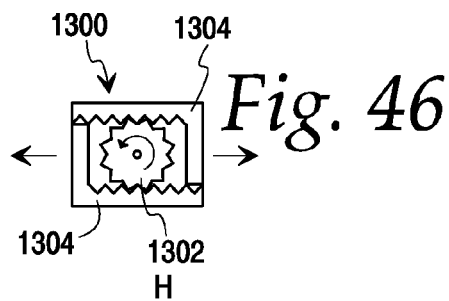
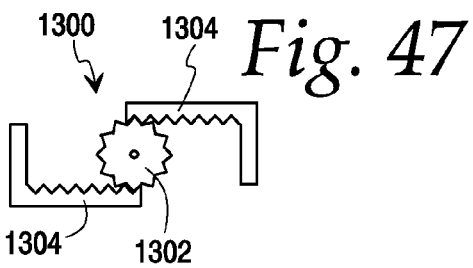
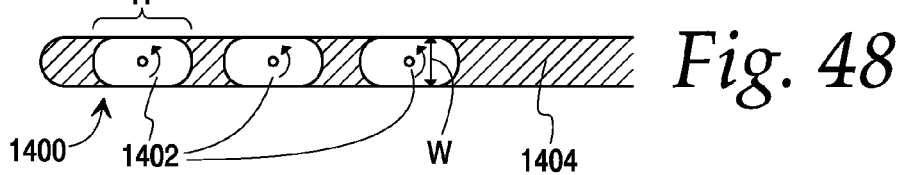
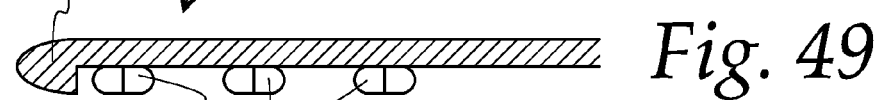
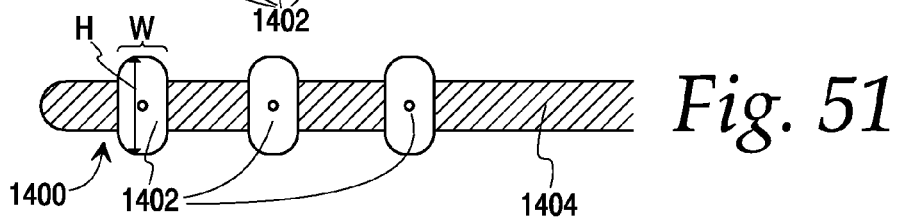
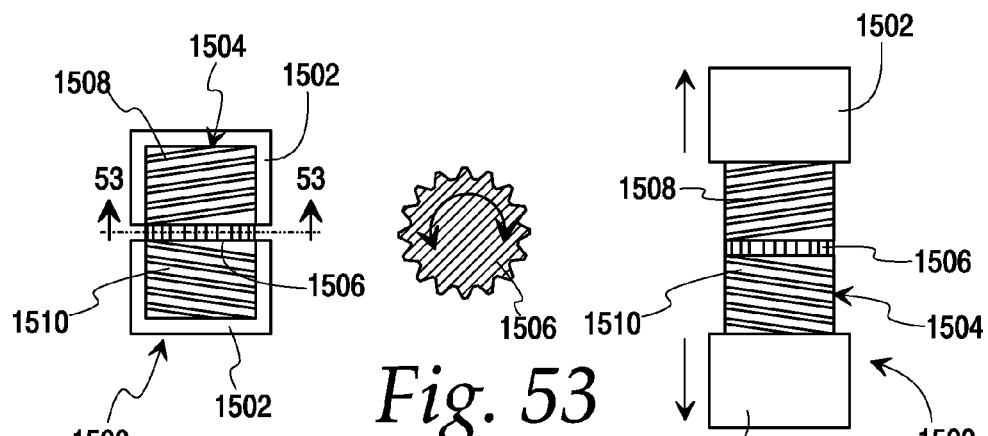
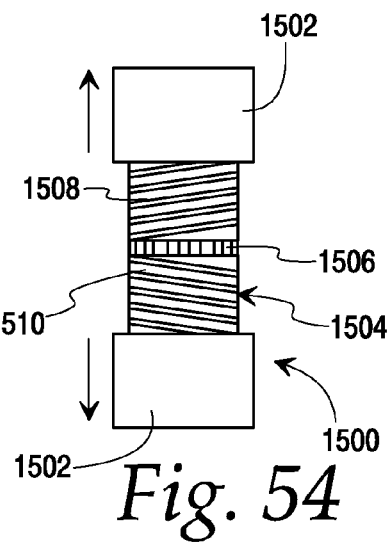

DISC SPACE SIZING DEVICES

CROSS-REFERENCE TO RELATED APPLICATIONS

This application is the U.S. national stage of international patent application no. PCT/US11/38377, filed May 27, 2011, which claims the benefit of U.S. provisional patent application No. 61/349,587, filed May 28, 2010, both of which are hereby incorporated herein by reference.

BACKGROUND

Field of the Disclosure

The present subject matter relates to devices for adjusting the spacing between adjacent vertebral bodies.

Description of Related Art

The spacing in the disc space between adjacent vertebral bodies may decrease for any of a number of reasons, including traumatic impacts and degenerative diseases. Improper spacing between adjacent vertebral bodies can lead to varying degrees of discomfort and/or pain and, if severe enough, may be reason for surgical correction of the spacing. Surgical correction often involves placement of an inter-body implant to support the vertebrae and restore the disc height to (or close to) its original height. To determine the proper size of the implant to place into the disc space, the current practice involves the use of traditional manual sizing paddles, which are often in the form shown in FIG. 1. Such known disc paddles S are generally oval-shaped, with one dimension H (referred to herein as its height) that is greater than another dimension W (referred to herein as its width). The distal end of the paddle S is inserted into the disc space in a flat orientation (i.e., with the plane of the paddle height H oriented parallel to the endplates of adjacent vertebral bodies) and then it is rotated 90° to re-orient the plane of the paddle height H perpendicular to the endplates. The height H of the paddle S is selected to equate to the proper separation between the adjacent vertebral bodies, such that the edges of the re-oriented paddle S contact the endplates and force proper spacing within the disc space. To accommodate different spacing situations, a set of paddles is typically provided with a variety of heights H, which may range from 8 mm to 14 mm in 1 mm increments.

One disadvantage to such an approach is that the means for delivering the distal end of the paddle S to the disc area (e.g., a working cannula) must be large enough to accommodate the height H and the width W. Accordingly, a relatively large delivery cannula or means is required to accommodate the larger-sized paddles. Larger paddles also require a larger access site, resulting in greater surgical resection and more retraction of nerve roots and other surrounding structures. This can lead to the possibility of greater trauma, loss of blood, and pain, as well as potentially increased surgical and recovery time. Nerve root retraction is one of the largest potential sources of patient harm in such procedures, and excessive retraction can lead to temporary or even permanent neural dysfunction. Another disadvantage is that each paddle is appropriate for only one separation amount, so if a particular paddle is initially used and found to result in improper spacing, it must be removed and the process repeated with a paddle having a different height. The multiple tool exchanges inherent in such an iterative sizing procedure increases the risk of damaging nerve roots or other surrounding structures.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a spacing device is provided for adjusting or measuring the spacing between adjacent vertebral bodies. The spacing device includes at least one distraction member movable between a first configuration for insertion into an intervertebral disc space and a second configuration in which the distraction member has a larger height dimension than in the first configuration for adjusting or measuring the spacing between adjacent vertebral bodies. The spacing device also includes an elongated actuator that translates along a longitudinal axis for moving the distraction member between the first configuration and the second configuration. A plurality of links pivotally connects the distraction member to the actuator. The distraction member includes outer and inner faces, with the outer face being configured to contact one of the adjacent vertebral bodies in the second configuration and the inner face facing the actuator. A monolithic distal portion of the actuator includes a plurality of enlarged portions spaced longitudinally along the longitudinal axis, with each enlarged portion comprising a pivot point pivotally connecting at least one of the links to the actuator and at least one of the enlarged portions including a proximal half that is substantially symmetrical to a distal half. The inner face of the distraction member defines a recess partially receiving one of the enlarged portions of the actuator when the distraction member is in the first configuration.

In another aspect, a spacing device is provided for adjusting or measuring the spacing between adjacent vertebral bodies. The device includes at least one distraction member that is moveable between a first configuration for insertion into an intervertebral disc space and a second configuration in which a height dimension of the distraction member is greater than in the first configuration for adjusting or measuring the spacing between adjacent vertebral bodies. The device includes an elongated actuator that translates along a longitudinal axis for moving the distraction member between the first configuration and the second configuration, with first and second pairs of links pivotally connecting the distraction member to the actuator. A monolithic distal portion of the actuator includes a plurality of enlarged portions spaced longitudinally along the longitudinal axis, with at least one of the enlarged portions including a proximal half that is substantially symmetrical to a distal half. Each pair of links includes a distal end pivotally connected to a different one of the enlarged portions of the actuator, with the first pair of links being fully positioned between proximal and distal ends of the distraction member when the distraction member is in the first configuration. The entire first pair of links is spaced longitudinally of the entirety of the second pair of links, and the actuator is configured for non-rotational movement along the longitudinal axis to move the distraction member between the first configuration and the second configuration.

A spacing device for adjusting or measuring the spacing between adjacent vertebral bodies, comprising: at least one distraction member movable between a first configuration for insertion into an intervertebral disc space and a second configuration in which the at least one distraction member has a larger height dimension than in the first configuration for adjusting or measuring the spacing between adjacent vertebral bodies; an elongated actuator that translates along a longitudinal axis for moving the at least one distraction member between the first configuration and the second configuration; and first and second pairs of links pivotally connecting the at least one distraction member to the actuator, wherein a monolithic distal portion of the actuator includes a plurality of enlarged portions spaced longitudinally along the longitudinal axis and each enlarged portion comprising a pivot pin pivotally connecting one of said pairs of links to the actuator, at least one of said enlarged portions includes a proximal half that is substantially symmetrical to a distal half of said at least one of said enlarged portions, the at least one distraction member includes proximal and distal ends and outer and inner faces, the outer face being configured to contact one of the adjacent vertebral bodies in the second configuration and the inner face facing the actuator and including a portion extending to a position between the first and second pairs of links, the first pair of links is fully positioned between the proximal and distal ends of the at least one distraction member when the at least one distraction member is in the first configuration, and the entire first pair of links is spaced longitudinally of the entirety of the second pair of links.

BRIEF DESCRIPTION OF THE DRAWINGS

FIG. 6 is a top view of another embodiment of a spacing device according to an aspect of the present disclosure, in an expanded configuration;

FIG. 7 is a top view of the spacing device of FIG. 6, in another expanded configuration;

FIG. 8 is a top view of another embodiment of a spacing device according to an aspect of the present disclosure, in a first configuration;

FIG. 9 is an end view of the spacing device of FIG. 8;

FIG. 10 is a top view of the spacing device of FIG. 8, in a fully expanded configuration;

FIG. 11 is an end view of the spacing device of FIG. 10;

FIG. 12 is an end view of the spacing device of FIG. 8, in a partially expanded configuration;

FIG. 13 is an end view of the spacing device of FIG. 8, in another partially expanded configuration;

FIG. 19 is a side view of another embodiment of a spacing device according to an aspect of the present disclosure, in a first or collapsed configuration;

FIG. 20 is a side view of the spacing device of FIG. 19, in a second or expanded configuration;

FIG. 21 is a side view of another embodiment of a spacing device according to an aspect of the present disclosure, in a first or collapsed configuration;

FIG. 22 is a side view of the spacing device of FIG. 21, in a second or expanded configuration;

FIG. 23 is a cross-sectional view of another embodiment of a spacing device according to an aspect of the present disclosure, in a first or collapsed configuration;

FIG. 24 is a cross-sectional view of the spacing device of FIG. 23, in an intermediate configuration;

FIG. 25 is a cross-sectional view of the spacing device of FIG. 23, in another intermediate configuration;

FIG. 26 is a cross-sectional view of the spacing device of FIG. 26, in a second or expanded configuration;

FIG. 27 is a perspective view of another embodiment of a spacing device according to an aspect of the present disclosure, in a first or collapsed configuration;

FIG. 28 is an end view of the spacing device of FIG. 27;

FIG. 29 is a cross-sectional view of the spacing device of FIG. 27, taken through the line 29-29;

FIG. 30 is a perspective view of the spacing device of FIG. 27, in an intermediate configuration;

FIG. 31 is a perspective view of the spacing device of FIG. 27, in another intermediate configuration;

FIG. 32 is an end view of the spacing device of FIG. 31;

FIG. 33 is a perspective view of the spacing device of FIG. 27, in a second or expanded configuration;

FIG. 34 is an end view of the spacing device of FIG. 33;

FIG. 35 is a side view of another embodiment of a spacing device according to an aspect of the present disclosure, in a first or collapsed configuration;

FIG. 36 is a side view of the spacing device of FIG. 35, in a second or expanded configuration;

FIG. 37 is a side view of another embodiment of a spacing device according to an aspect of the present disclosure, in a first or collapsed configuration;

FIG. 38 is a side view of the spacing device of FIG. 37, in a second or expanded configuration;

FIG. 39 is a perspective view of another embodiment of a spacing device according to an aspect of the present disclosure, in a first or collapsed configuration;

FIG. 40 is an end view of the spacing device of FIG. 39;

FIG. 41 is a perspective view of the spacing device of FIG. 39, in a second or expanded configuration;

FIG. 42 is an end view of the spacing device of FIG. 41;

FIG. 43 is a top view of another embodiment of a spacing device according to an aspect of the present disclosure, in a second or expanded configuration;

FIG. 44 is an end view of the spacing device of FIG. 43, in a first or collapsed configuration;

FIG. 45 is an end view of the spacing device of FIG. 43;

FIG. 46 is an end view of another embodiment of a spacing device according to an aspect of the present disclosure, in a first or collapsed configuration;

FIG. 47 is an end view of the spacing device of FIG. 46, in a second or expanded configuration;

FIG. 48 is a side view of another embodiment of a spacing device according to an aspect of the present disclosure, in a first or collapsed configuration;

FIG. 49 is a top view of a first version of the spacing device of FIG. 48;

FIG. 50 is a top view of a second version of the spacing device of FIG. 48;

FIG. 51 is a side view of the spacing device of FIG. 48, in a second or expanded configuration;

FIG. 52 is a side view of another embodiment of a spacing device according to an aspect of the present disclosure, in a first or collapsed configuration;

FIG. 53 is a cross-sectional view of the spacing device of FIG. 52, taken through the line 53-53; and FIG. 54 is a side view of the spacing device of FIG. 52, in a second or expanded configuration.

DESCRIPTION OF THE ILLUSTRATED EMBODIMENTS

The embodiments disclosed herein are for the purpose of providing the required description of the present subject matter. They are only exemplary, and may be embodied in various forms. Therefore, specific details disclosed herein are not to be interpreted as limiting the subject matter as defined in the accompanying claims.

Figure 1:
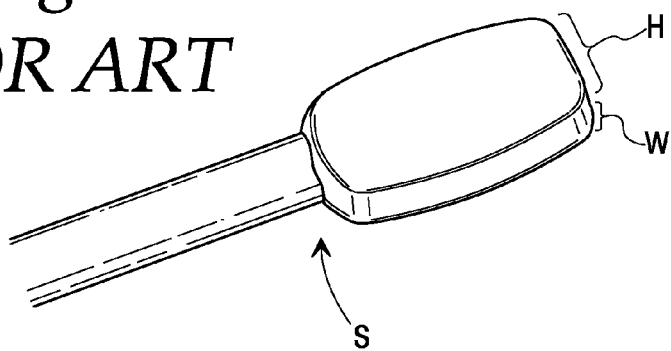
FIG. 1 is a perspective view of a known prior disc paddle.
Figure 2:
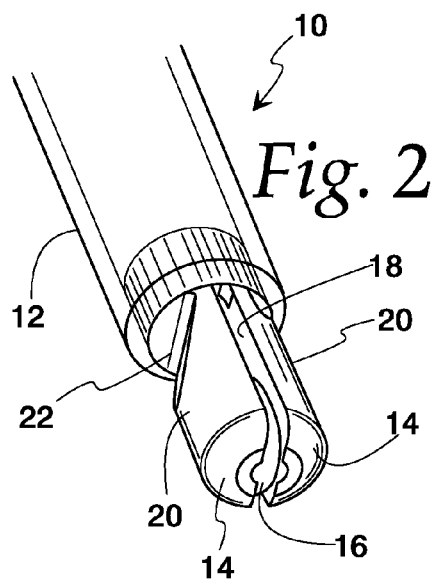
FIG. 2 is a perspective view of a spacing device according to an aspect of the present disclosure, in a first or collapsed configuration.

FIGS. 2-54 show exemplary embodiments of spacing devices according to the present disclosure. The spacing devices described herein are advantageous in that they have a small initial, first, or "collapsed" profile (e.g., in the range of approximately 6-8 mm in width and in height) when entering a target disc space, but are movable (by operation of an actuator) to a different or second configuration having a larger profile (e.g., in the range of approximately 8-15 mm) which is suitable for spacing apart two vertebral bodies in preparation for implantation of an intervertebral body fusion implant or cage. The small initial profile permits the use of a minimally invasive percutaneous entry to the spinal disc space by known standard working cannula of the type well known in the spinal surgery field. The intra-operative height in many of the illustrated embodiments is infinitely adjustable anywhere between the fully collapsed minimum size to a fully expanded maximum size. Thus, in these embodiments, a single device offers the advantage of providing a range of different distraction sizes, unlike known devices, wherein each paddle is capable of only one distraction size. Further, as will be described in greater detail below, the handles of devices according to the present disclosure may convey the status of the spacing device (e.g., the height of the device) with visual markings or other means, thereby obviating the need for intra-operative imaging techniques to visualize the distal end of the device.

According to one embodiment, illustrated in FIGS. 2-5, a spacing device 10 includes a handle or shaft 12, a pair of outer sizing or distraction jaws or members 14 cooperatively associated with a distal end of the handle or shaft 12, and an inner distraction member, such as a wedge or paddle 16 positioned intermediate the jaws 14. For purposes of this description, "sizing or distraction jaws or members" are not limited to a particular function or device configuration, but are intended to include any structure(s) suitable for insertion into a cavity, space, or region between body tissues (e.g., in the disc space between adjacent vertebral bodies) for the purpose of ascertaining the actual or desired separation between the tissues and/or moving the body tissues away from each other to or toward the desired separation therebetween. While a number of devices which are suitable for such applications are described herein, such embodiments are merely exemplary of the concepts and functions arising from and employed in this disclosure.

Each jaw 14 has an inner surface 18 (which faces the inner surface 18 of the other jaw 14) and a preferably atraumatic outer surface 20. In one embodiment, the jaws 14 are comprised of a flexible material, such as a flexible polymer, and may be provided with a notched portion 22 adjacent to the distal end of the handle shaft 12 to create a live or living hinge. Preferably, but not exclusively, the jaws 14 are biased to a closed configuration. The distraction member or paddle 16) has a height dimension H that is greater than its width dimension W and is rotatable with respect to the jaws 14.

Figure 3:
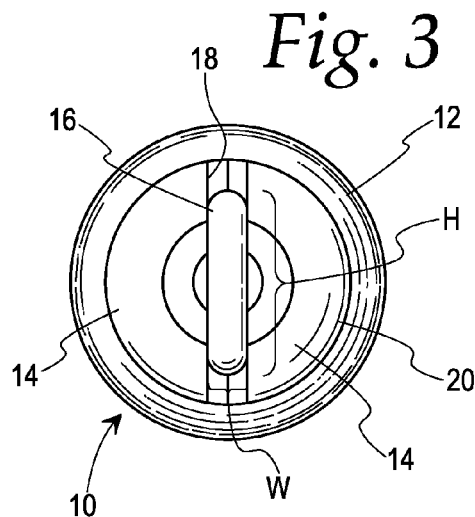
FIG. 3 is an end view of the spacing device of FIG. 2.

In use, the distal end of the spacing device 10 with paddle 16 and jaws 14 is delivered to a target disc space in an initial or collapsed or first configuration shown in FIGS. 2 and 3. In this configuration, the distal end of the spacing device 10 has a small profile or first height dimension, such as approximately 6 mm in height and in width. The distal end of the spacing device 10 may be oriented in such direction as desired—such as shown in FIG. 3, with the larger height dimension H of the paddle 16 extending vertically and the smaller width dimension W extending horizontally. As used herein, the term "vertically" refers to a direction generally the same as, parallel to, or coaxial with the axis of the spine, while the term "horizontally" refers to a direction generally perpendicular to the axis of the spine.

Figure 4:
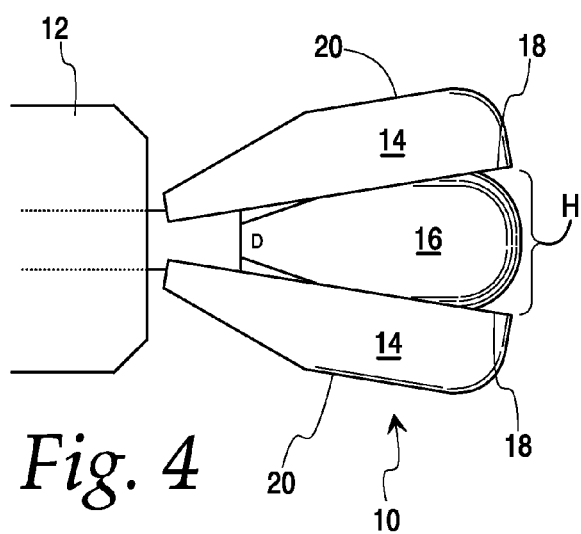
FIG. 4 is a top view of the spacing device of FIG. 2, in a second or expanded configuration.
Figure 5:
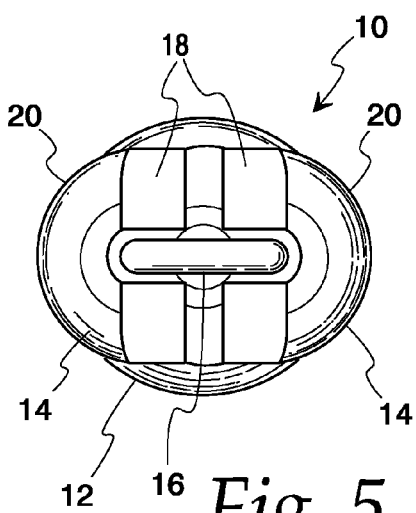
FIG. 5 is an end view of the spacing device of FIG. 4.

When the distal end of the spacing device 10 is properly positioned, the paddle 16 is rotated to the desired angle, such as 90°, about its central axis. Doing so causes the larger height dimension H of the paddle 16 to bear against the inner surfaces 18 of the jaws 14, pressing them outwardly to a second or expanded or open configuration (FIGS. 4 and 5). In this configuration, the distal end of the spacing device 10 has a maximum profile or second height dimension which is larger than in the collapsed configuration, such as up to approximately 9 mm. The spacing device 10 may be provided with an indicator (e.g., visual markings on the handle shaft 12) to display the separation of the jaws 14 (i.e., whether they are in the closed configuration of FIGS. 2 and 3 or the open configuration of FIGS. 4 and 5 and to what degree or amount that they are open).

With the distal end of the spacing device 10 in the expanded configuration, the jaws 14 and paddle 16 are jointly rotated 90° about the central axis of the paddle 16, which causes the enlarged profile to bear against the vertebral body endplates and spread them to the proper separation. Alternatively, rather than expanding the jaws 14 horizontally and then rotating them in combination with the paddle 16 to contact the endplates, the jaws 14 may be expanded vertically to directly distract the endplates. Thereafter, after the vertebral bodies are properly separated, further operations may be performed within the target disc space (e.g., implanting an intervertebral body fusion implant or cage).

When all operations within the target disc space have been completed, the paddle 16 is again rotated 90° about its central axis with respect to the jaws 14. This causes the larger height dimension H of the paddle 16 to move out of contact with the inner surfaces 18 of the jaws 14, which allows the jaws 14 to resiliently return to their initial configuration and the spacing device 10 to return to its initial small configuration (FIGS. 2 and 3). Finally, the spacing device 10 is removed from the target disc space.

To achieve different opening sizes, a series of differently sized paddles may be provided, similar to known practice. However, in contrast to known methods, a given paddle may achieve a substantially greater separation because of the presence of the jaws 14 of FIGS. 2-5, which add to the opening size. For example, a set of paddles having a height dimension H in the range of approximately 1-6 mm may be used to achieve a full device opening height in the range of approximately 8-14 mm.

Alternatively, the spacing device 10 of FIGS. 2-5 may be modified to include a mechanism for adjusting the longitudinal position of the paddle, as shown in FIGS. 6 and 7. In the spacing device 100 of FIGS. 6-7, the paddle 102 is positioned at the end of a lever arm 104 which is longitudinally movable with respect to the jaws or distraction members 106. The spacing device 100 may include a component (e.g., a threaded rod in the handle) for precisely adjusting the longitudinal position of the paddle 102. So adjusting the position of the paddle 102 changes the contact point of the paddle 102 on the inside surfaces 108 of the jaws 106 when the spacing device 100 is in the expanded or open configuration. If the paddle 102 is extended a relatively large distance D (FIG. 6), the jaw profile J will be smaller than when the paddle 102 is extended a smaller distance D' (FIG. 7). For example, in the configuration of FIG. 6 the paddle extension distance D is approximately 7.5 mm, resulting in a jaw profile J of approximately 11 mm. By comparison, in the configuration of FIG. 7, the paddle extension distance D' is approximately 5.5 mm, resulting in a jaw profile J' of approximately 12 mm. Hence, it will be appreciated that a wide variety of jaw profiles may be achieved with just one spacing device 100.

Another variation to the embodiment of FIGS. 2-5 is illustrated in FIGS. 8-13. The spacing device 150 of FIGS. 8-13 is similar to the spacing device 10 of FIGS. 2-5, in that it includes a handle or shaft 152, a pair of outer sizing or distraction jaws or members 154 connected to a distal end of the handle or shaft 152, and an inner distraction member, provided as a wedge or paddle 156 positioned intermediate the jaws 154. The distraction member or paddle 156 has a height dimension H that is greater than its width dimension W and is rotatable with respect to the jaws 154, as described above with regard to the embodiment of FIGS. 2-5. As also described above, each jaw 154 has an inner surface 158 (which faces the inner surface 158 of the other jaw 154) and a preferably atraumatic outer surface 160. Rather than being connected to the shaft 152 by a living hinge, each jaw 154 is connected to the shaft 152 via a link or hinge 162. In contrast to the embodiments of FIGS. 2-7, the hinges 162 allow the jaws 154 to remain parallel with each other and the endplates when moved from their initial closed or collapsed configuration (FIGS. 8 and 9) to their open or expanded configuration (FIGS. 10-13). A benefit of this design is that it allows for parallel contact with the endplates (FIG. 10), thereby resulting in a larger contact area between the jaws 154 and the endplates during a distraction procedure.

In use, the distal end of the spacing device 150 with paddle 156 and jaws 154 is delivered to a target disc space in an initial or collapsed or closed configuration shown in FIGS. 8 and 9. In this configuration, the distal end of the spacing device 150 has a small profile or first height dimension. When the distal end of the spacing device 150 is properly positioned, the paddle 156 is rotated to a desired non-zero angle about its central axis. Doing so causes the larger height dimension H of the paddle 156 to bear against the inner surfaces 158 of the jaws 154, pressing them outwardly to a more expanded or open configuration (FIGS. 10-13). The spacing device 150 may be provided with an indicator (e.g., visual markings on the handle shaft 152) to display the separation of the jaws 154 and/or a locking mechanism (e.g., a ratchet or detent element) to maintain the paddle 156 at the selected angle.

FIGS. 10 and 11 illustrate a "fully open" or "fully expanded" configuration, with the paddle 156 rotated 90° about its central axis. In this configuration, the spacing device 150 has a maximum profile height or second height dimension which is larger than in the collapsed configuration. With the spacing device 150 in the expanded configuration, the jaws 154 and paddle 156 are jointly rotated 90° about the central axis of the paddle 156, which causes the enlarged profile to bear against the vertebral body endplates and spread them to the proper separation. Alternatively, rather than expanding the jaws 154 horizontally and then rotating them in combination with the paddle 156 to contact the endplates, the jaws 154 may be expanded vertically to directly distract the endplates. Thereafter, after the vertebral bodies are properly separated, further operations may be performed within the target disc space (e.g., implanting an intervertebral body fusion implant or cage).

As in the embodiments of FIGS. 2-7, the paddle 156 is not limited to a 90° rotation angle, but may be rotated to an angle between 0° and 90°. For example, FIG. 12 illustrates the paddle 156 rotated to an approximately 45° angle, while FIG. 13 illustrates the paddle 156 rotated to an approximately 60° angle. At relatively low angles, the profile of the jaws 154 will be relatively small (down to the minimum profile illustrated in FIGS. 8 and 9), whereas at greater angles, the profile of the jaws 154 will be greater (up to the maximum profile illustrated in FIGS. 10 and 11). The paddle 156 may be rotated to any angle between 0° and 90°, thereby making the profile of the jaws 154 infinitely adjustable between the minimum profile (FIGS. 8 and 9) and the maximum profile (FIGS. 10 and 11), in a range of heights between 6 and 12 mm or more.

When all operations within the target disc space have been completed, the paddle 156 is again rotated about its central axis with respect to the jaws 154 to return the spacing device 150 to its initial small configuration (FIGS. 8 and 9). Finally, the distal end of the spacing device 150 is removed from the target disc space.

Figure 14:
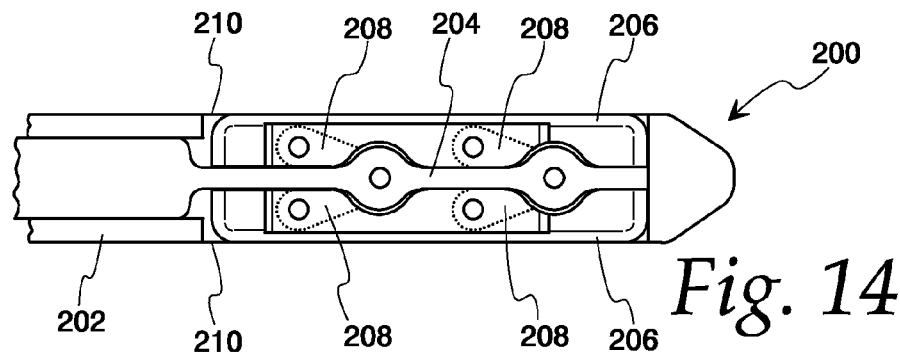
FIG. 14 is a cross-sectional view of another embodiment of a spacing device according to an aspect of the present disclosure, in a first or collapsed configuration.
Figure 15:
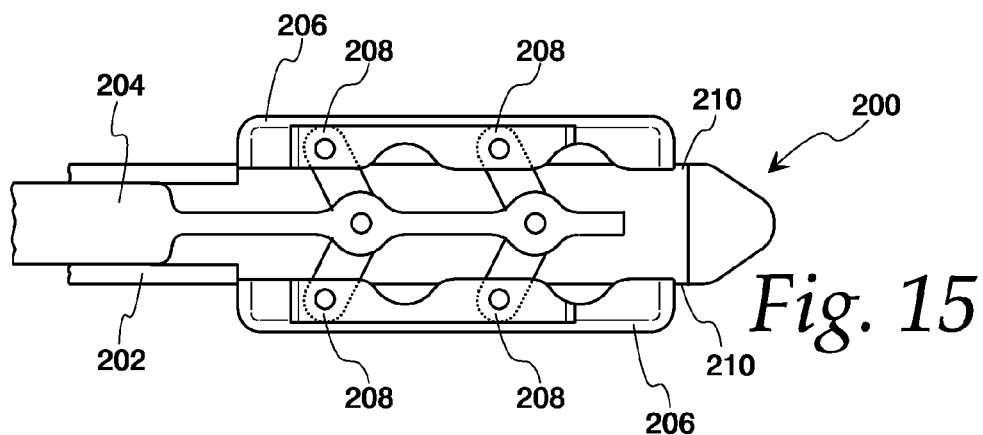
FIG. 15 is a cross-sectional view of the spacing device of FIG. 14, in a second or expanded configuration.

According to another embodiment, illustrated in FIGS. 14 and 15, a spacing device 200 includes a hollow delivery member or cannula 202, a slider member 204 received within the delivery member 202, and a pair of spacer contacts or elements 206 each pivotally associated with the slider member 204 by a pair of links 208 and having opposed surfaces for contacting vertebral end plates facing the disc space. The delivery member 202 includes lateral windows or cutouts 210 aligned with the distraction members 206, which accommodate the distraction members 206 when they are moved from a first or initial configuration (FIG. 14) to a second or expanded configuration (FIG. 15), as will be described in greater detail below.

In use, the distal end of the spacing device 200 is positioned so as to locate the distraction members 206 within a target disc space. The spacing device 200 is initially in the collapsed configuration shown in FIG. 14, with the distraction members 206 contained within the delivery member 202 for a small profile or first height dimension.

When the distraction members 206 are properly positioned, the slider member 204 is moved proximally (i.e., retracted), which causes the proximal ends of the distraction members 206 to bear against the proximal edge of the associated window 210 and pivot outwardly to protrude through the windows 210 (FIG. 15). It will be seen that, in this expanded configuration, the maximum profile height of the spacing device 200 is greater than in the initial configuration of FIG. 14. The spacing device 200 may be provided with a locking mechanism or interlock to lock the slider member 204 (and, hence, the distraction members 206) in the expanded configuration during use.

The distraction members 206 may be either expanded horizontally and the spacing device 200 rotated 90° to bear against the adjacent vertebral body endplates or expanded vertically to directly distract the endplates to the proper separation. Thereafter, further operations may be performed within the target disc space (e.g., implanting an intervertebral body fusion implant or cage).

When all operations within the target disc space have been completed, the slider member 204 is moved distally, which causes the distal ends of the distraction members 206 to bear against the distal edge of the associate window 210 and pivot inwardly to the initial configuration of FIG. 14. Finally, the distal end of the spacing device 200 is removed from the target disc space.

Figure 16:
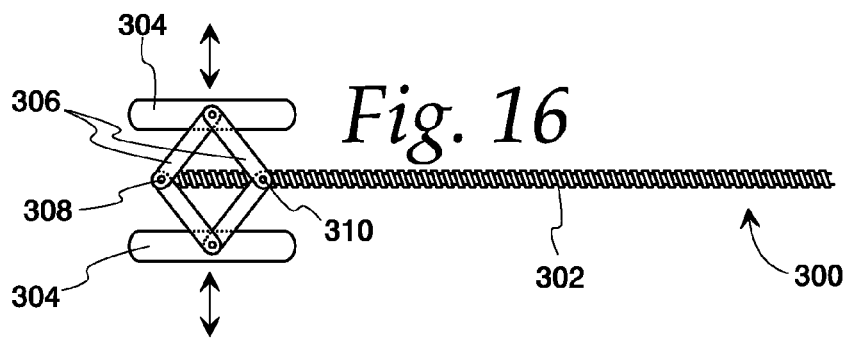
FIG. 16 is a side view of another embodiment of a spacing device according to an aspect of the present disclosure.

Variations of the link-based spacing device of FIGS. 14 and 15 are also possible. For example, FIG. 16 shows a spacing device 300 in the nature of a scissors jack. The spacing device 300 includes a threaded shaft 302, a pair of distraction members 304, and a set of links 306 pivotally associating the threaded shaft 302 and the distraction members 304. The spacing device 300 may include additional components, such as a hollow delivery member or cannula (not illustrated) similar to the one shown in FIGS. 14 and 15.

The threaded shaft 302 is rotatable with respect to the link connection points 308 and 310. The distal connection point 308 is longitudinally fixed with respect to the threaded shaft 302 (i.e., it will not move along the length of the shaft 302 when the shaft 302 is rotated), whereas the proximal connection point 310 is movable along the length of the shaft 302 when the shaft 302 is rotated, such as by a threaded coupling or follower. Accordingly, the distance between the link connection points 308 and 310 may be adjusted, which has the effect of adjusting the separation between the distraction members 304 (i.e., the maximum profile or height dimension of the distal end of the spacing device 300). A locking device or interlock may be employed to selectively prevent the shaft 302 from rotating.

In use, the distal end of the spacing device 300 is positioned so as to locate the distraction members 304 within a target disc space. The spacing device 300 is initially in a first or collapsed configuration, with the link connection points 308 and 310 at a maximum separation distance and the distraction members 304 at a minimum separation distance for a small profile or first height dimension.

When the distraction members 304 are properly positioned, the threaded shaft 302 is rotated about its central axis to move the link connection points 308 and 310 closer together and increase the separation distance between the distraction members 304. The distraction members 304 may be either expanded horizontally and then rotated 90° to bear against the vertebral body endplates or expanded vertically to directly distract the endplates to the proper separation. Thereafter, further operations may be performed within the target disc space (e.g., implanting an intervertebral body fusion implant or cage).

When all operations within the target disc space have been completed, the shaft 302 is rotated about its central axis in the opposite direction to move the distraction members 304 to their initial configuration and the spacing device 300 is removed from the target disc space.

Figure 17:
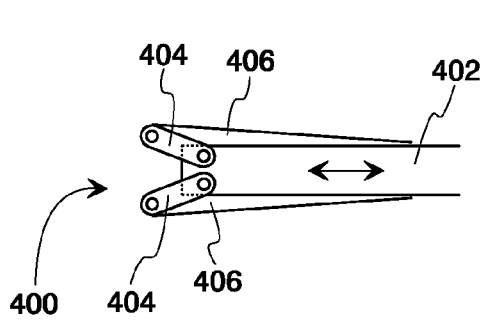
FIG. 17 is a side view of another embodiment of a spacing device according to an aspect of the present disclosure, in a first or collapsed configuration.
Figure 18:
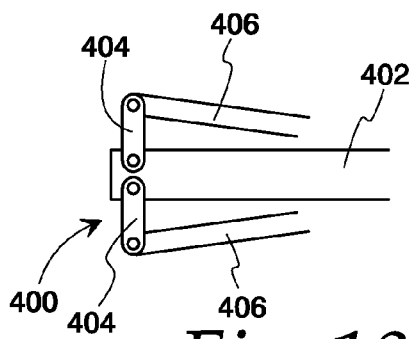
FIG. 18 is a side view of the spacing device of FIG. 17, in a second or expanded configuration.

FIGS. 17 and 18 show another embodiment of a link-based spacing device 400. The distal end of the spacing device 400 includes an elongated base bar 402, a pair of links 404 pivotally connected at their inner ends to the base bar 402, and a pair of elongated expansion bars 406 pivotally connected to the outer ends of the links 404. The spacing device 400 may include additional components, such as a delivery lumen or the like.

The links 404 are movable between an initial or collapsed or closed configuration having a relatively small profile or first height dimension (FIG. 17) and an expanded or open configuration having a larger profile or second height dimension (FIG. 18). To place the links 404 in the collapsed configuration, the expansion bars 406 are pressed distally to position the links 404 generally longitudinally. When the expansion bars 406 are moved proximally with respect to the base bar 402, the links 404 will pivot outwardly to define a greater profile (FIG. 18). A stop mechanism may be employed to prevent the expansion bars 406 from moving farther proximally than illustrated in FIG. 18 (which would have the effect of decreasing the profile of the links 404).

In use, the distal end of the spacing device 400 is positioned so as to locate the links 404 within a target disc space. The spacing device 400 is initially in a collapsed configuration, with the links 404 extending generally longitudinally for a small profile or first height dimension (FIG. 17).

When the links 404 are properly positioned, the expansion bars 406 are moved proximally with respect to the base bar 402 to rotate the links 404 outwardly to the expanded configuration or second height dimension of FIG. 18. The links 404 may be either expanded horizontally and then rotated 90° to bear against the adjoining vertebral body endplates or expanded vertically to directly distract the endplates to the proper separation. Thereafter, further operations may be performed within the target disc space (e.g., implanting an intervertebral body fusion implant or cage).

When all operations within the target disc space have been completed, the expansion bars 406 are moved distally with respect to the base bar 402 to move the links 404 to their initial configuration and the distal end of the spacing device 400 is removed from the target disc space.

FIGS. 19 and 20 show yet another embodiment of a link-based spacing device 500. The distal end of the spacing device 500 includes a pair of distraction members 502 pivotally connected to each other by a pair of links 504. While the distraction members 502 are illustrated as being relatively short, one or both may be elongated to allow for direct manipulation by an operator. The spacing device 500 may include additional components, such as a delivery lumen or the like.

The distraction members 502 are pivotally movable between an initial or collapsed or closed configuration having a relatively small profile or first height dimension (FIG. 19) and an expanded or open configuration having a larger profile or second height dimension (FIG. 20). To place the distraction members 502 in the collapsed configuration, they are moved out of alignment with each other (i.e., with one being moved distally of the other until the two press against each other). When the distraction members 502 are moved into alignment with each (i.e., at the same longitudinal location), the links 504 will be at an acute angle of selected degree, up to perpendicular to the distraction members 502 (FIG. 20), placing the distraction members 502 in an expanded configuration with a larger profile. A locking or stop mechanism or interlock may be employed to selectively maintain the links 504 and distraction members 502 in the selected expanded configuration.

In use, the distal end of the spacing device 500 is positioned so as to locate the distraction members 502 within a target disc space. The spacing device 500 is initially in a collapsed configuration, with the distraction members 502 in close proximity or pressing against each other for a small profile or first height dimension (FIG. 19).

When the distraction members 502 are properly positioned, the links 504 are pivoted to place the distraction members 502 into longitudinal alignment with each other to assume the expanded configuration or second height dimension of FIG. 20. The distraction members 502 may be either expanded horizontally and then rotated up to 90° to bear against the vertebral body endplates or expanded vertically to directly distract the endplates to the proper separation. Thereafter, further operations may be performed within the target disc space (e.g., implanting an intervertebral body fusion implant or cage).

When all operations within the target disc space have been completed, the distraction members 502 are moved back into contact with each other (to assume the initial configuration of FIG. 19) and the distal end of the spacing device 500 is removed from the target disc space.

FIGS. 21 and 22 show a spacing device 600 with a distal end including a series of linked bars or supports 602, referred to herein as "links." The end of each link 602 pivotally attached to an end of the adjacent links 602. Additional components may also be employed without departing from the scope of the present disclosure.

The links 602 are pivotally movable between an initial or collapsed configuration having a relatively small profile or first height dimension (FIG. 21) and an expanded configuration having a larger profile or second height dimension (FIG. 22). To place the links 602 in the collapsed configuration, a proximally directed force is applied to the proximal-most link(s) 602 (FIG. 21), which pulls the links 602 into a straight, substantially longitudinal line (or lines in the embodiment of FIGS. 21 and 22) for a minimum profile. When a distally directed force is applied to the proximal-most link(s) 602, the links 602 will pivot about their ends to press against each other in a "stack" (FIG. 22) wherein the links 602 are oriented at an angle up to substantially transverse to the axis of the spacing device 600 for a maximum profile expanded configuration.

In use, the distal end of the spacing device 600 is positioned so as to locate the links 602 within a target disc space. The spacing device 600 is initially in a collapsed configuration, with the links 602 in the orientation of FIG. 21.

When the links 602 are properly positioned, a distally directed or compressive force is applied to move the links 602 into the expanded "stack" configuration of FIG. 22. The links 602 may be either expanded horizontally and the spacing device 600 rotated 90° to bear against the vertebral body endplates or expanded vertically to directly distract the endplates to the proper separation. Thereafter, further operations may be performed within the target disc space (e.g., implanting an intervertebral body fusion implant or cage).

When all operations within the target disc space have been completed, a proximally directed or tensional force is applied to the links 602 to move them back into the initial configuration of FIG. 21 and the distal end of the spacing device 600 is removed from the target disc space.

FIGS. 23-26 show a wedge-activated spacing device 700, which includes a hollow delivery member or cannual 702, a slider member 704 received within the delivery member 702, and a pair of distraction members 706 cooperatively associated with a distal end of the spacing device 700. The delivery member 702 includes lateral windows or cutouts aligned with the distraction members 706, which accommodate the distraction members 706 when they are moved from an initial configuration or first height dimension (FIG. 23) to an expanded configuration or second height dimension (FIG. 26), as will be described in greater detail below. A locking member or interlock 708 engages the distraction members 706 in the initial configuration to prevent them from inadvertently moving to the expanded configuration.

In use, the distal end of the spacing device 700 is positioned so as to locate the distraction members 706 within a target disc space. The spacing device 700 is initially in a configuration of reduced cross-sectional dimension ("collapsed configuration") shown in FIG. 23, with the distraction members 706 contained within the delivery member 702 for a small profile or first height dimension.

When the distraction members 706 are properly positioned, the slider member 704 is moved distally, causing it to contact the locking member 708. This moves the locking member 708 distally, which disengages it from the distraction members 706 (FIG. 24). Further advancing the slider member 704 brings the inclined distal surfaces of the slider member 704 into contact with the inclined proximal surfaces of the distraction members 706. This moves the distraction members 706 outwardly (through the windows) and brings the slider member 704 to nest between the distraction members 706, such as in a tongue-and-groove relationship (FIGS. 25 and 26), which provides support to maintain separation between the distraction members 706. In one embodiment, the slider member 704 also contacts and moves the locking member 708 distally to seat between the distraction members 706 to provide additional support for the distraction members 706 in the expanded configuration (FIG. 26).

The distraction members 706 may be either expanded horizontally and the spacing device 700 rotated 90° to bear against the vertebral body endplates or expanded vertically to directly distract the endplates to the proper separation. Thereafter, further operations may be performed within the target disc space (e.g., implanting an intervertebral body fusion implant or cage).

When all operations within the target disc space have been completed, the slider member 704 is moved proximally, which causes the locking member 708 to automatically collapse the distraction members 706 and ultimately lock the distraction members 706 in the initial configuration of FIG. 23. Finally, the distal end of the spacing device 700 is removed from the target disc space.

Variations of the wedge-type spacing device of FIGS. 23-26 are also possible. For example, FIGS. 27-34 show an alternative wedge-type spacing device 800. The spacing device 800 includes a hollow delivery member or cannula 802, a slider member 804 received within the delivery member 802, and a pair of distraction members 806 cooperatively associated with the distal end of the spacing device 800. As illustrated in FIG. 28 the distraction members 806 may include an interlock which, in one embodiment, comprises interlocking features 808 and 810. In the illustrated embodiment, a female dovetail slot 808 of one of distraction members 806 receives a male dovetail rail 810 when the spacing device 800 is in its collapsed configuration (FIG. 27). The rail 810 is thinner than the slot 808 and the two are slidably movable relative to each other, such that the rail 810 can freely move into, along, and out of the slot 808 (FIG. 32) as the distraction members 806 move toward and away from each other. The slider member 804 includes a similar rail 812 and slot 814 (FIG. 29), although the rail 812 of the slider member 804 is configured to substantially fill the slot 808 of the distraction member 806, while the slot 814 of the slider member 804 is configured to be substantially filled by the rail 810 of the distraction member 806 when the spacing device 800 is in an expanded configuration (FIG. 34). The components of the spacing device 800 may be made from a variety of materials, including PEEK (polyetheretherketone).

In use, the distal end of the spacing device 800 is positioned within a target disc space. The spacing device 800 is initially in the collapsed or reduced transverse configuration shown in FIG. 27, with the distraction members 806 contained within the delivery member 802 for a small profile or first height profile.

When the distal end of the spacing device 800 is properly positioned, the delivery member 802 is retracted and/or the slider member 804 is moved distally to cause the distraction members 806 to extend outside of the delivery member 802. The distraction members 806 may be prevented from detaching from the remainder of the spacing device 800 by anchoring mechanisms, such as tethers or the like (not illustrated).

The slider member 804 is then moved distally, which brings the inclined distal surfaces 804a of the slider member 804 into contact with the inclined proximal surfaces 806a of the distraction members 806 (FIG. 31). This begins to move the distraction members 806 away from each other, with the slot 808 and rail 810 of the distraction members 806 separating from each other (FIG. 32) while the slot 814 and rail 812 of the slider member 804 begin to interlock with the corresponding rail 810 and slot 808 of the distraction members 806.

Further movement of the slider member 804 in the distal direction fully interlocks its slot 814 and rail 812 with the corresponding rail 810 and slot 808 of the distraction members 806 (FIG. 34) and fully distracts the distraction members 806 to the maximum profile (FIGS. 33 and 34). In this expanded configuration, the spacing device 800 has a second height dimension or profile which is nearly twice as large as its first height dimension or profile in the initial configuration of FIG. 27. The distraction members 806 may be either expanded horizontally and then rotated 90° to bear against the vertebral body endplates or expanded vertically to directly distract the endplates to the proper separation. Thereafter, further operations may be performed within the target disc space (e.g., implanting an intervertebral body fusion implant or cage).

When all operations within the target disc space have been completed, the slider member 804 is moved proximally, which allows the distraction members 806 to collapse toward each other. The distraction members 806 may then be returned into the delivery member 802 for removal of the distal end of the spacing device 800 from the target disc space in the collapsed configuration of FIG. 27.

FIGS. 35 and 36 show another wedge-type spacing device 900. The distal end of the spacing device 900 includes a threaded shaft 902, a pair of distraction members 904, and a pair of wedge members 906 associated with the shaft 902 and the distraction members 904. The wedge members 906 are interlocked to the distraction members 904 by any suitable means, such as the joint-slot configuration described in reference to the embodiment of FIGS. 27-34 to prevent relative rotation between the wedge members 906 and distraction members 904. The spacing device 900 may include additional components without departing from the scope of the present disclosure.

The threaded shaft 902 is rotatable with respect to the wedge members 906 and includes oppositely threaded sections 908 and 910. Alternatively, the shaft 902 could be threaded in one direction and the wedge members 906 threaded in opposed directions. As a result, rotation of the shaft 902 about its axis will cause the wedge members 906 to move longitudinally along the shaft 902, either toward or away from each other. Moving the wedge members 906 toward each other will bring their inclined surfaces 906a to bear against the inclined surfaces 904a of the distraction members 904, causing the distraction members 904 to move away from each other, thereby increasing the profile of the spacing device 900 (FIG. 36). Conversely, rotating the shaft 902 so as to cause the wedge members 906 to move away from each other will result in the distraction members 904 moving toward each other, ultimately to the minimum profile configuration shown in FIG. 35. The distraction members 904 in this embodiment, as in other embodiments, may be biased, as by a spring or other member, to a position of reduced cross-sectional profile.

In use, the distal end of the spacing device 900 is positioned so as to locate the distraction members 904 within a target disc space. The spacing device 900 is initially in a collapsed configuration (FIG. 35), with the wedge members 906 preferably at a maximum separation distance and the distraction members 904 at a minimum separation distance for a small profile or first height dimension.

When the distraction members 904 are properly positioned, the threaded shaft 902 is rotated about its central axis to move the wedge members 906 closer together and increase the separation distance between the distraction members 904 to a desired larger profile or second height dimension. The distraction members 904 may be either expanded horizontally and then rotated 90° to bear against the vertebral body endplates or expanded vertically to directly distract the endplates to the proper separation. Thereafter, further operations may be performed within the target disc space (e.g., implanting an intervertebral body fusion implant or cage).

When all operations within the target disc space have been completed, the shaft 902 is rotated about its central axis in the opposite direction to move the distraction members 904 to their initial configuration and the distal end of the spacing device 900 is removed from the target disc space.

FIGS. 37 and 38 show yet another alternative spacing device 1000. The spacing device 1000 includes a pair of spacer arms or distraction members 1002 pivotally connected to a frame member or cannula 1004 and a wedge member 1006 at a distal end of an elongated member such as a positioning rod 1008. In the illustrated embodiment, the spacer arms 1002 have a generally arcuate or dogleg shape which combine to accommodate a wedge member such as the spherical wedge member 1006. The spacer arms 1002 and wedge member 1006 may have different shapes without departing from the scope of the present disclosure. Further, additional components may be provided (e.g., a spring or resilient member to bias the spacer arms 1002 toward each other) without departing from the scope of the present disclosure.

In use, the distal end of the spacing device 1000 is positioned so as to locate the spacer arms 1002 within a target disc space. The spacing device 1000 is initially in a collapsed configuration (FIG. 37), with the wedge member 1006 out of contact with the spacer arms 1002 and the spacer arms 1002 pivoted toward each other for a small profile or first height dimension.

When the spacer arms 1002 are properly positioned, the wedge member 1006 is moved proximally (e.g., by retracting the positioning rod 1008) to contact the spacer arms 1002 and pivot them away from each other to an expanded configuration or larger second height dimension, such as shown in FIG. 38. The spacer arms 1002 may be either expanded horizontally and then rotated 90° to bear against the vertebral body endplates or expanded vertically to directly distract the endplates to the proper separation. The arm surfaces, as with the distraction member surfaces in the other embodiments, that bear against the endplates may have endplate-engaging surfaces of any suitable shape or size and contour. Thereafter, further operations may be performed within the target disc space (e.g., implanting an intervertebral body fusion implant or cage).

When all operations within the target disc space have been completed, the wedge member 1006 is moved distally, out of contact with the spacer arms 1002 to allow the spacer arms 1002 to pivot back toward each other (FIG. 37). Finally, with the distal end of the spacing device 1000 in its initial configuration, it is removed from the target disc space.

FIGS. 39-42 illustrate a rotary-actuated spacing device 1100. The spacing device 1100 includes a hollow delivery member or cannula 1102, an elongated rotation member 1104 received within the delivery member 1102, and a pair of distraction members 1106 each pivotally associated with the rotation member 1104. The delivery member 1102 includes access apertures such as arcuate windows or cutouts 1108 through which the distraction members 1106 extend when they are moved from an initial configuration (FIGS. 39 and 40) to an expanded configuration (FIGS. 41 and 42), as will be described in greater detail below.

In use, the distal end of the spacing device 1100 is positioned so as to locate the distraction members 1106 within a target disc space. Only a small aperture, the size of the delivery member 1102 is required for access into the disc space. The spacing device 1100 is initially in the collapsed configuration shown in FIGS. 39 and 40, with the distraction members 1106 substantially contained within the delivery member 1102 for a small profile or first height dimension.

When the distraction members 1106 are properly positioned, the delivery member 1102 and rotation member 1104 are relatively rotated (clockwise in the illustrated embodiment), which causes the edges of the windows 1108 to bear against the edges of the associated distraction member 1106 and pivot the distraction members 1106 outwardly until they are extending radially through the windows 1108 (FIGS. 41 and 42). It will be seen that, in this expanded configuration, the maximum profile or second height dimension of the spacing device 1100 is substantially greater than in the initial configuration of FIGS. 39 and 40. The spacing device 1100 may be provided with a locking mechanism or interlock to lock the rotation member 1104 (and, hence, the distraction members 1106) in the expanded configuration during use.

The distraction members 1106 may be either expanded horizontally and the spacing device 1100 rotated 90° to bear against the vertebral body endplates or expanded vertically to directly distract the endplates to the proper separation. Thereafter, further operations may be performed within the target disc space (e.g., implanting an intervertebral body fusion implant or cage).

When all operations within the target disc space have been completed, the delivery member 1102 is rotated about its central axis (counterclockwise in the illustrated embodiment), which causes the edges of the windows 1108 to bear against the edge of the associate distraction member 1106 and pivot the distraction members 1106 inwardly to the initial configuration of FIGS. 39 and 40. Finally, the distal end of the spacing device 1100 is removed from the target disc space.

In an alternative embodiment of the spacing device 1100 of FIGS. 39-42, the distal end of a spacing device 1200 is provided with a rotation member with opposed pivot connection points, such as a generally flat or planar rotation member 1202 (FIGS. 43-45) instead of a cylindrical rotation member. The spacing device 1200 includes a flat, generally cross-sectionally C-shaped rotation member 1202, and a pair of flat, generally "C-shaped" distraction members 1204 each pivotally associated with the rotation member 1202 by a pin 1206. The spacing device 1200 may also include a hollow delivery member or cannula comparable in structure and operation to the one shown in FIGS. 39-42, for example, with windows or cutouts through which the distraction members 1204 extend when they are moved between a collapsed configuration (FIG. 44) and an expanded configuration (FIGS. 43 and 45).

In use, the distal end of the spacing device 1200 is positioned so as to locate the distraction members 1204 within a target disc space. The spacing device 1200 is initially in the collapsed configuration shown in FIG. 44, with the distraction members 1204 folded against each other and/or the rotation member 1202 for a small profile or first height dimension.

When the distraction members 1204 are properly positioned, the rotation member 1202 is rotated (counterclockwise in the illustrated embodiment), which causes the distraction members 1204 to pivot into linear alignment with the rotation member 1202 (FIGS. 43 and 45). It will be seen that, in this expanded configuration, the maximum profile of the spacing device 1200 is greater than in the initial configuration of FIG. 44. The spacing device 1200 may be provided with a locking mechanism to lock the rotation member 1202 (and, hence, the distraction members 1204) in the expanded configuration during use.

The distraction members 1204 may be either expanded horizontally and the spacing device 1200 rotated 90° to bear against the vertebral body endplates or expanded vertically to directly distract the endplates to the proper separation. Thereafter, further operations may be performed within the target disc space (e.g., implanting an intervertebral body fusion implant or cage).

When all operations within the target disc space have been completed, the rotation member 1202 is rotated about its central axis (clockwise in the illustrated embodiment), which causes the distraction members 1204 to fold toward each other and/or the rotation member 1202 to the initial configuration of FIG. 44. Finally, the distal end of the spacing device 1200 is removed from the target disc space.

FIGS. 46 and 47 show the paddle mechanism of another alternative spacing device 1300, which includes an internal gear 1302 and a pair of toothed distraction members 1304 to interact in rack-and-pinion fashion. It will be understood that the spacing device 1300 may include additional components, such as a delivery member or cannula for retaining and delivering the paddle mechanism to a target disc space.

The teeth of the gear 1302 and the distraction members 1304 are engaged and oriented such that rotation of the gear 1302 about its central axis will cause the distraction members 1304 to move toward or away from each other, between an initial or collapsed configuration having a small profile or first height dimension (FIG. 46) and an expanded configuration having a larger profile or second height dimension (FIG. 47). In the illustrated embodiment, rotating the gear 1302 counterclockwise will tend to move the distraction members 1304 toward each other, while rotating the gear 1302 clockwise will tend to move the distraction members 1304 away from each other. A ratcheting or clutching mechanism may be provided to prevent inadvertent movement of the distraction members 1304 toward each other upon application of a compressive force (e.g., during use in a disc-spacing procedure), effectively locking the spacing device 1300 in the expanded configuration or even in a partially expanded configuration.

In use, the distal end of the spacing device 1300 is positioned so as to locate the distraction members 1304 within a target disc space. The spacing device 1300 is initially in the collapsed configuration shown in FIG. 46, with distraction members 1304 relatively close to each other for a small profile or first height dimension.

When the distraction members 1304 are properly positioned, the gear 1302 is rotated clockwise to move the distraction members 1304 away from each other and into the expanded configuration of FIG. 47. The distraction members 1304 may be either expanded horizontally and then rotated 90° to bear against the vertebral body endplates or expanded vertically to directly distract the endplates to the proper separation. Thereafter, further operations may be performed within the target disc space (e.g., implanting an intervertebral body fusion implant or cage).

When all operations within the target disc space have been completed, the gear 1302 is rotated counterclockwise to move the distraction members 1304 toward each other, ultimately to the initial configuration of FIG. 46. Finally, the distal end of the spacing device 1300 is removed from the target disc space.

FIGS. 48-51 show a spacing device 1400 with a distal end having multiple distraction members 1402 spaced apart from each other along an elongated member or frame 1404. The spacing device 1400 further includes a push rod or pull wire or other actuator (not illustrated) for selectively rotating the distraction members 1402 (either alone or simultaneously) with respect to the frame 1404. Additional components, delivery devices (such as a cannula), and others may be provided without departing from the scope of the present disclosure.

The distraction members 1402 may be positioned along the same side of the frame 1404 (FIG. 49) or on opposite sides of the frame 1404 (FIG. 50). Each distraction member 1402 has a height dimension H that is greater than a width dimension W. The height of the frame 1404 is less than the height H of the distraction members 1402, such that the orientation of the distraction members 1402 may be manipulated to increase the profile of the spacing device 1400 (FIG. 51), as will be described in greater detail herein.

In use, the distal end of the spacing device 1400 is positioned so as to locate the distraction members 1402 within a target disc space. The spacing device 1400 is initially in a collapsed configuration (FIG. 48), with each distraction member 1402 oriented so that its height dimension H extends longitudinally for a small profile or first height dimension.

When the distraction members 1402 are properly positioned, they are rotated up to 90° or at another selected angle with respect to the frame 1404 to an expanded configuration in which their height dimension H extends transverse to the axis of the frame 1404 (FIG. 51), resulting in a larger profile or second height dimension. The distraction members 1402 may be either expanded horizontally and the spacing device 1400 rotated 90° to bear against the vertebral body endplates or expanded vertically to directly distract the endplates to the proper separation. Thereafter, further operations may be performed within the target disc space (e.g., implanting an intervertebral body fusion implant or cage).

When all operations within the target disc space have been completed, the distraction members 1402 are rotated 90° back to the initial configuration of FIG. 48 and the distal end of the spacing device 1400 is removed from the target disc space.

FIGS. 52-54 show the paddle mechanism at the distal end of a spacing device 1500, with distraction members 1502 in the form of end caps associated with a threaded core 1504 having a rotation actuator or gear 1506 (FIG. 53). It will be understood that the spacing device 1500 includes additional components, such as a delivery member for retaining and delivering the paddle mechanism to a target disc space.

The core 1504 is rotatable with respect to the distraction members 1502 by operation of the gear 1506 and includes oppositely threaded sections 1508 and 1510. As a result, rotation of the core 1504 about its axis will cause the distraction members 1502 to move along the core 1504, either toward or away from each other. Moving the distraction members 1502 toward each other will decrease the profile of the spacing device 1500 to a collapsed or initial configuration (FIG. 52). Conversely, rotating the core 1504 so as to cause the distraction members 1502 to move away from each other will increase the profile of the spacing device 1500 to an expanded configuration (FIG. 54).

In use, the distal end of the spacing device 1500 is positioned so as to locate the distraction members 1502 within a target disc space. The spacing device 1500 is initially in a collapsed configuration (FIG. 52), with the distraction members 1502 relatively close to each other for a small profile or first height dimension.

When the distraction members 1502 are properly positioned, the gear 1506 is actuated to rotate the core 1504 and move the distraction members 1502 away from each other, to the expanded configuration or larger second height dimension of FIG. 54. The distraction members 1502 may be either expanded horizontally and then rotated 90° to bear against the vertebral body endplates or expanded vertically to directly distract the endplates to the proper separation. Thereafter, further operations may be performed within the target disc space (e.g., implanting an intervertebral body fusion implant or cage).

When all operations within the target disc space have been completed, the gear 1506 is actuated in the reverse direction to rotate the core 1504 and return the distraction members 1502 to their initial configuration (FIG. 52). Finally, the distal end of the spacing device 1500 is removed from the target disc space.

Spacing devices according to the present disclosure may be comprised of standard medical-grade materials, such as nylon, polycarbonate, relatively rigid polymer or stainless steel, which are sufficiently durable to withstand biomechanical forces experienced during use of the device, as well as sufficiently inexpensive for disposal after one-time use. Alternatively, the devices may be constructed of materials which are suitable for cleaning and re-sterilization for subsequent re-use, as is common with similar instruments for spine surgery. They may also include non-mechanical components (e.g., a pressure transducer and associated control system to identify the compressive force of the disc space and use that information to dictate the expanded profile of the device) without departing from the scope of the present disclosure.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A spacing device for adjusting or measuring the spacing between adjacent vertebral bodies, comprising:

at least one distraction member movable between a first configuration for insertion into an intervertebral disc space and a second configuration in which the at least one distraction member has a larger height dimension than in the first configuration for adjusting or measuring the spacing between adjacent vertebral bodies;

an elongated actuator that translates along a longitudinal axis for moving the at least one distraction member between the first configuration and the second configuration; and a plurality of links pivotally connecting the at least one distraction member to the actuator, wherein the at least one distraction member includes outer and inner faces, the outer face being configured to contact one of the adjacent vertebral bodies in the second configuration and the inner face facing the actuator, a monolithic distal portion of the actuator includes a plurality of enlarged portions spaced longitudinally along the longitudinal axis and each enlarged portion comprising a pivot point pivotally connecting at least one of said links to the actuator and at least one of said enlarged portions including a proximal half that is substantially symmetrical to a distal half, and the inner face of the at least one distraction member defines a recess partially receiving one of the enlarged portions of the actuator when the at least one distraction member is in the first configuration.

2. A spacing device according to claim 1, wherein the height dimension of the at least one distraction member is infinitely adjustable between the height dimension of the at least one distraction member in the first configuration and the height dimension of the at least one distraction member in the second configuration.

3. A spacing device according to claim 1, wherein the at least one distraction member comprises a pair of distraction members movable toward and away from each other in moving between the first configuration and the second configuration.

4. A spacing device according to claim 3, wherein the actuator for moving the at least one distraction member between the first configuration and the second configuration is movable between the pair of distraction members.

5. A spacing device according to claim 3, wherein each distraction member includes an inner face defining a recess partially receiving said one of the enlarged portions of the actuator when the distraction members are in the first configuration.

6. A spacing device according to claim 1, wherein the actuator is longitudinally movable with respect to the at least one distraction member.

7. A spacing device according to claim 1, further comprising a delivery cannula including a distal-facing surface configured to contact a proximal end of the at least one distraction member when the at least one distraction member is moved from the first configuration to the second configuration.

8. A spacing device according to claim 1, wherein
the inner face of the at least one distraction member defines a second recess partially receiving another one of the enlarged portions of the actuator when the at least one distraction member is in the first configuration.

9. A spacing device according to claim 1, wherein
the at least one distraction member includes proximal and distal ends, and the plurality of links are fully positioned between the proximal and distal ends of the at least one distraction member when the at least one distraction member is in the first configuration.

10. A spacing device according to claim 1, wherein
the at least one distraction member includes proximal and distal ends, and at least one of the links is fully positioned between the proximal and distal ends of the at least one distraction member when the at least one distraction member is in the first configuration.

11. A spacing device for adjusting or measuring the spacing between adjacent vertebral bodies, comprising:

at least one distraction member movable between a first configuration for insertion into an intervertebral disc space and a second configuration in which the at least one distraction member has a larger height dimension than in the first configuration for adjusting or measuring the spacing between adjacent vertebral bodies;

an elongated actuator with a longitudinal axis for moving the at least one distraction member between the first configuration and the second configuration; and first and second pairs of links pivotally connecting the at least one distraction member to the actuator, wherein a monolithic distal portion of the actuator includes a plurality of enlarged portions spaced longitudinally along the longitudinal axis, at least one of said enlarged portions includes a proximal half that is substantially symmetrical to a distal half of said at least one of said enlarged portions, each pair of links includes a distal end pivotally connected to a different one of the enlarged portions of the actuator, the at least one distraction member includes proximal and distal ends, the first pair of links is fully positioned between the proximal and distal ends of the at least one distraction member when the at least one distraction member is in the first configuration, the entire first pair of links is spaced longitudinally of the entirety of the second pair of links, and the actuator is configured for non-rotational movement along the longitudinal axis to move the at least one distraction member between the first configuration and the second configuration.

12. A spacing device according to claim 11, wherein the height dimension of the at least one distraction member is infinitely adjustable between the height dimension of the at least one distraction member in the first configuration and the height dimension of the at least one distraction member in the second configuration.

13. A spacing device according to claim 11, wherein the at least one distraction member comprises a pair of distraction members movable toward and away from each other in moving between the first configuration and the second configuration.

14. A spacing device according to claim 13, wherein the actuator for moving the at least one distraction member between the first configuration and the second configuration is movable between the pair of distraction members.

15. A spacing device according to claim 11, wherein the actuator is longitudinally movable with respect to the at least one distraction member.

16. A spacing device according to claim 11, further comprising a delivery cannula including a distal-facing surface configured to contact a proximal end of the at least one distraction member when the at least one distraction member is moved from the first configuration to the second configuration.

17. A spacing device according to claim 11, wherein the second pair of links is fully positioned between the proximal and distal ends of the at least one distraction member when the at least one distraction member is in the first configuration.

18. A spacing device for adjusting or measuring the spacing between adjacent vertebral bodies, comprising:
  at least one distraction member movable between a first configuration for insertion into an intervertebral disc space and a second configuration in which the at least one distraction member has a larger height dimension than in the first configuration for adjusting or measuring the spacing between adjacent vertebral bodies;
  an elongated actuator that translates along a longitudinal axis for moving the at least one distraction member between the first configuration and the second configuration; and
  first and second pairs of links pivotally connecting the at least one distraction member to the actuator, wherein
  a monolithic distal portion of the actuator includes a plurality of enlarged portions spaced longitudinally along the longitudinal axis and each enlarged portion comprising a pivot pin pivotally connecting one of said pairs of links to the actuator,
  at least one of said enlarged portions includes a proximal half that is substantially symmetrical to a distal half of said at least one of said enlarged portions,
  the at least one distraction member includes proximal and distal ends and outer and inner faces, the outer face being configured to contact one of the adjacent vertebral bodies in the second configuration and the inner face facing the actuator and including a portion extending to a position between the first and second pairs of links,
  the first pair of links is fully positioned between the proximal and distal ends of the at least one distraction member when the at least one distraction member is in the first configuration, and
  the entire first pair of links is spaced longitudinally of the entirety of the second pair of links.

* * * * *